United States Patent [19]

Zahler et al.

[11] Patent Number: 5,130,348
[45] Date of Patent: Jul. 14, 1992

[54] POLYETHER IMPRESSION MATERIALS CONTAINING POLYALKYLENE OXIDE DERIVATIVES

[75] Inventors: Wolf-Dietrich Zahler, Hechendorf; Oswald Gasser; Klaus Ellrich, both of Seefeld, all of Fed. Rep. of Germany

[73] Assignee: THERA Patent GmbH & Co., KG, Seefeld, Fed. Rep. of Germany

[21] Appl. No.: 580,595

[22] Filed: Sep. 11, 1990

[30] Foreign Application Priority Data

Mar. 10, 1989 [DE] Fed. Rep. of Germany ....... 3932989

[51] Int. Cl.$^5$ .................. A61K 6/10; C08G 73/00; C08G 73/04
[52] U.S. Cl. .................................... 523/109; 528/424; 525/403
[58] Field of Search ............... 523/109, 427, 439, 436; 528/424, 322, 290, 361; 525/403

[56] References Cited

U.S. PATENT DOCUMENTS

| | | | |
|---|---|---|---|
| 3,453,242 | 7/1969 | Schmitt et al. | 528/322 |
| 4,167,618 | 9/1979 | Schmitt et al. | 528/424 |
| 4,493,911 | 1/1985 | Schmitt et al. | 523/109 |
| 4,657,959 | 4/1987 | Bryan et al. | 524/266 |
| 4,670,485 | 6/1987 | Hess et al. | 523/436 |
| 4,778,832 | 10/1988 | Futami et al. | 523/109 |
| 4,867,790 | 9/1989 | Jochum et al. | 523/109 |
| 4,877,854 | 10/1989 | Hattori et al. | 528/15 |

OTHER PUBLICATIONS

Polymer Blends vol. 1 Editor D. R. Paul 1978 p. 89.
Polymer-Polymer Miscibility-Olabisi et al. 1979 pp. 243, 244, 249, and 343.

Primary Examiner—John Kight, III
Assistant Examiner—Shelley Wright
Attorney, Agent, or Firm—Birch, Stewart, Kolasch & Birch

[57] ABSTRACT

There is disclosed a polyether impression material containing
(a) a polyether,
(b) a catalyst, and
(c) a mixing additive, in which the components (a) and (b) are spatially separate from each other, and in which the mixing additive (c) is polyalkylene oxide derivative with a molecular weight above 300, which is chemically inert with the other components present and in particular, does not contain hydroxyl groups, acid groups, primary amino groups, ionic groups, halogen groups or groups capable of polymerization. The composition can be mixed easily, has outstanding storage stability and does not dissociate even under increased pressure.

6 Claims, No Drawings

POLYETHER IMPRESSION MATERIALS CONTAINING POLYALKYLENE OXIDE DERIVATIVES

FIELD OF THE INVENTION

The present invention relates to polyether impression materials containing polyalkylene oxide derivatives.

BACKGROUND OF THE INVENTION

Silicones, alginates and hydrocolloids are used in the production of working models in dental engineering and also in the production of precise impressions and temporary dental prostheses in dentistry. For example, U.S. Pat. No. 4,778,832 describes silicone compositions, which contain hydrophilic silicone oils or non-ionic surfactants to make the compositions hydrophilic. As non-ionic surfactants, inter alia, polyethers and partial esters of polyalcohols and fatty acids come into consideration.

For particularly precise work, polyether impression materials are used. Such impression materials generally consist of polyalkylene oxides, in which the end groups are derivatized with polymerizable compounds. For example, the U.S. Pat. Nos. 3,453,242 and 4,093,555, DE-PS-1 544 837 and DE-OS 32 46 654, describe aziridine-containing polyalkylene oxides for this use. The aziridine containing compounds are generally used in conjunction with fillers, colorants and other auxiliary agents, such as, for example, plasticizers.

For the initiation of the polymerization reaction, e.g., from U.S. Pat. No. 4,167,618, sulphonium salts are known, which contain an electron-attracting group in the beta-position to the central sulfur atom and a non-nucleophilic anion.

So-called plasticizers and solubilizers are usually added to the aziridine-containing compounds and the component which contains the catalyst to regulate the processing properties and the plastic/elastic behavior. Hydroxy-functional poly-alkylene oxides, such as the copolymers of ethylene oxide and propylene oxide, phthalates, such as, e.g., dioctyl phthalate, citrates, such as e.g., acetyl trialkyl citrate, and toluene and dibenzyl toluene have, for example, been described for this use.

The use of such compounds is also known from other fields. For example, British Patent reference GB-PS 621 104 describes the use of polyalkylene oxides and polyalkylene oxide glycols as surfactants in dye dispersions and the like. German Patent reference DE-OS 37 12 646 explains the use of alkyl-polyalkylene carboxyl compounds as essential constituents in skin-care preparations and German Patent reference DE-OS 37 02 178 refers to the use of polyglycerine ethers as skin-compatible additives in cosmetic and pharmaceutical preparations.

The polyether impression materials are usually stored in the form of two spatially separate components until they are actually used. The reactive impression material is then formed by intensive mixing and hardens in a few minutes. Here one component contains the polyether, e.g., the aziridine-containing compound, and the other component the catalyst, e.g, the sulphonium salts. Since relatively high-molecular-weight compounds are used in the first component and relatively low-molecular-weight compounds are used in the second, the mixture ratio usually differs clearly from a mixture ratio of 1:1, even when fillers and plasticizers and also solubilizers are added.

To mix the components, in addition to mixing with a spatula on a block, the dentist has mechanical mixing aids available to him. Centrifuge mixers are known for this purpose on the one hand and on the other, it is known for the components to be homogeneously mixed with each other by static mixing. In this case, the two components are stored in double-chamber cartridges and shortly before use, are pressed through a mixing nozzle in which a static mixing element is housed. The components are mixed with each other due to the special form of the mixing spirals. In this system, the flow properties of the two components must be as similar as possible, and in addition, their chemical behavior should be so similar that immediate mixing takes place with short contact times.

To adjust a mixture ratio in polyether impression materials as would be suitable to be mixed with static mixers, it was often necessary to introduce relatively large amounts of fillers and plasticizers and/or solubilizers into the component containing the catalyst. However, with the known plasticizers and/or solubilizers, this was only partly possible because problems of storage instability occurred, particularly dissociation of the mixture, or the rheological behavior of the two components differed notably, or the two components differed chemically to such an extend that they could not be homogeneously mixed in a static mixer.

SUMMARY OF THE INVENTION

Accordingly, an object of the invention is to prepare a polyether impression material in which the rheological and chemical behavior of the two components is matched so that optimum mixing is achieved in mixing nozzles with a static mixing element. It is also an object of the present invention to be able to incorporate large amounts of plasticizers and/or solubilizers and fillers into the components, without there being a negative effect on either the physical end-properties of the hardened material or the flow properties of the admixed components.

The subject of the present invention is a poly-ether impression material containing
(a) a polyether,
(b) a catalyst,
(c) a mixing additive, and
(d) optionally usual additives,
in which the components (a) and (b) are spatially separate from each other, and the mixing additive (c) is a polyalkylene oxide derivative with a molecular weight over 300, which is chemically inert with the other components present and in particular contains no hydroxyl groups, acid groups, primary amino groups, ionic groups, halogen groups or groups capable of polymerization.

DETAILED DESCRIPTION OF THE INVENTION

In the present invention, polyalkylene oxide is understood to refer to a homo- or copolymer of one or more different alkylene oxides. In the case of copolymers, the monomers can be arranged regularly or irregularly alternating, however, a homopolymer can also be produced initially from an alkylene oxide and is then "grafted" with one or more monomers (alkylene oxides).

Preferably, polyalkylene oxide derivatives of the general Formula I are used in the present invention:

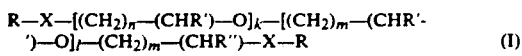

in which:
n = 1 to 6, preferably 1 to 4, particularly 1, and n can vary within the chain;
m = 1 to 6, preferably 1 to 4, particularly 3, and m can vary within the chain;
k,l = 2 to 500, preferably 4 to 250, particularly 10 to 200;
R', R" = H, methyl, ethyl, preferably R' and R" are H;
X = S, O, NH, preferably O;
R = $C_{1-18}$-, preferably $C_{1-12}$-, particularly $C_{1-6}$-alkyl, or carbonyl-$C_{1-17}$-, preferably carbonyl-$C_{1-11}$-, particularly carbonyl-$C_{1-5}$-alkyl, or a radical of the general Formula II:

R''' = $C_{1-18}$-, preferably $C_{1-12}$-, particularly preferably $C_{1-6}$-alkyl and/or -aryl and X has the meaning indicated above,
with the proviso that bracketed expressions indexed with the symbols k and l can be arranged in a regularly or irregularly alternating form, or in a block form.

Formula I describes compounds containing a polyalkylene oxide skeleton, which means, the component between the two groupings X in Formula I. It can be a homo- or copolymerizate of alkylene oxides, such as ethylene oxide, popylene oxide, tetrahydrofuran, trioxetane, etc. Copolymers of ethylene oxide and tetrahydrofuran are preferred for forming the skeleton.

The copolymers encompassed hereby can have a regularly and irregularly alternating structure. The homo- or copolymers used preferably have average molecular weights between 300 and 20,000, particularly preferably between 500 and 10,000. Production takes place in a manner known per se by cationic polymerization of the alkylene oxides, for example, with catalysts of the type $BF_3$ or $BF_3$-etherate. Homo- or copolymers with hydroxyl end groups usually occur, these can however be converted in a manner known per se into SH- or $NH_2$-end groups. The group X in combination with a hydrogen atom represents the end group of the polyalkylene oxide. This can be an OH-group, an SH-group or an $NH_2$-group, which are then reacted with compounds RH by etherification or esterification reactions and by reaction with isocyanates or by means of multi-stage reactions, such as the reaction with phosgene and amines. The compounds of Formula I are preferably the reaction products of polyalkylene oxides (with hydroxyl end groups) with aliphatic monocarboxylic oxides with formic acid, acetic acid, propionic acid and butyric acid.

The polyalkylene oxide derivative to be used according to the present invention is preferably in the component which contains the catalyst, preferably the sulphonium salt.

The polyethers (a) contain a polyalkylene oxide skeleton, such as was defined in the mixing additive (c), but with reactive end groups, e.g., aziridine end groups, which are capable of polymerization on addition of the catalyst (b).

As the polyethers (a), the aziridine-containing polyalkylene oxide compounds are preferably used as are described, e.g., in U.S. Pat. Nos. 3,453,242 and 4,093,555. As the catalysts (b), the sulphonium salts known from U.S. Pat. No. 4,167,618 are preferred.

The quantity of the polyether or the preferred aziridine compound, calculated relative to the total mass of the two components, is preferably 20 to 80% by weight, particularly preferably 32 to 60% by weight and particularly 45 to 55% by weight.

The catalyst and in particular, the preferred sulphonium salts are preferably used in amounts of 0.2 to 24% by weight, particularly preferably 1 to 18% by weight, particularly 5 to 15% by weight, relative to the weight of the total mass.

The polyalkylene oxide derivatives to be used according to the invention are used in amounts of preferably 2 to 60% by weight, particularly preferably 8 to 50% by weight, and particularly 10 to 40% by weight, relative to the total weight.

The polyether impression materials can in addition contain fillers and thixotropy promoters to produce a paste-like consistency. Suitable fillers, are, for example, quartzes, $CaCO_3$, diatomites and pyrogenic silica. It can be advantageous to treat the surfaces of the fillers. Suitable surface-treatment agents are silanes, such as, e.g., hexamethyl disilazane.

Moreover, in addition to the polyalkylene oxide derivatives, according to the present invention, further plasticizers and/or solvents, as are already known, can be used.

The additives (fillers, plasticizers, solvents, etc.) are used together in amounts of 0 to 70% by weight, preferably 10 to 50% by weight, particularly preferably 20 to 40% by weight, relative to the weight of the total mass.

The compositions according to the invention are particularly suitable for use in static mixers.

EXAMPLE 1

160 g of a copolymer of ethylene oxide and tetrahydrofuran (in the ratio 1:1, molecular weight approx. 3,000) are stirred up with 80 g of cyclohexane and 130 mg of dibutyl tin dilaurate into a homogeneous clear solution. 5.8 g of butyl isocyanate are added at 23° C. and the reaction mixture stirred for 1 hour, the temperature climbing to approximately 30° C. After the reaction mixture has returned to ambient temperature, stirring is continued for another 24 hours at ambient temperature, following which excess isocyanate and cyclohexane is distilled off. A quantitative yield of polyalkylene-oxide dibutyl-urethane is obtained.

EXAMPLE 2

The reaction is carried out in an analogous way to Example 1, but utilizing 6 g of cyclohexyl isocyanate (instead of butyl isocyanate). The heat of reaction reaches 31° C. after 1 hour; stirring is continued for 24 hours at ambient temperature and again excess isocyanate and solvent are distilled off. A quantitative yield of the polyalkylene-oxide bicyclohexyl-urethane is obtained.

EXAMPLE 3

600 g of a copolymer of THF and ethylene oxide (in the ratio 2:1, molecular weight 6,000) are dissolved in 1.3 liters of cyclohexane. Following this 35.2 g of butyric acid and 3.5 g of toluene sulfonic acid are added and heated for 20 hours under reflux and with simultaneous separation of water. Extraction is then carried out three times with 200 ml of 2nNaOH in each case and one time with $2nH_2SO_4$ and then two times with 200 ml of $H_2O$. The mixture is then dried over sodium sulphate and the residual solvent is distilled off. 500 g of polyalkylene-oxide dibutyrate are obtained as the yield.

EXAMPLE 4

The reaction is carried out in an analogous way to Example 3, with acetic anhydride, 19.4 g (instead of butyric acid), heating for 4 hours under influx. Following this, as in Example 3, heating is continued for 10 hours with simultaneous separation of water. Further processing takes place as in Example 3, by means of a double extraction with aqueous caustic soda (2n), one time extraction with aqueous sulphuric acid (2n) and double extraction with distilled $H_2O$. The mixture is then dried again with sodium sulphate and the solvent distilled off. 500 g of polyalkylene-oxide diacetate is obtained.

APPLICATION EXAMPLE 100 parts by weight of a polyether with aziridino end groups (average molecular weight approx. 6,500), the production of which is described in U.S. Pat. No. 3,453,742 (Example 13), are kneaded into a homogeneous paste with 5 parts by weight of acetyl tributyl citrate and 40 parts by weight of fine diatomite. The paste is referred to below as the base paste.

50 parts by weight of acetyl tributyl citrate, 50 parts by weight of dibenzyl toluene and 40 parts by weight of beta(S-lauryl-S-ethyl-sulphonium)-butyronitrile-fluoroborate are mixed, accompanied by gentle heating until a homogeneous clear solution forms. 50 parts by weight of this solution are kneaded in each case into a homogeneous paste with 40 parts by weight of fine diatomite and with the amounts of mixing additives indicated in the following table. The paste is referred to in the following as the catalyst paste.

Equal parts by weight of base and catalyst paste are pressed through a static mixer (Keller Prozesstechnik Co.), comprising a cylinder with a length of 60 mm and a diameter of 5 mm and a static mixer with 13 mixture elements, and the mixing result evaluated. The results are reproduced in the following Table.

TABLE

| Experiment Number | Mixing additive [wt % in catalyst paste] | Mixing quality | Storage stability |
|---|---|---|---|
| 1 (comparison) | — | Highly marbled, in part no bonding into the different layers | Stable |
| 2 (comparison) | Polyethylene oxide (OH-end groups) (Fluka Co., molecular weight 2,000) [25 wt %] | Clearly marbled, in part no bonding into the different layers | Separates under pressure |
| 3 (according to invention) | polyalkylene-oxide dibutyl-urethane (Production Example 1) [25 wt %] | Good, no separable layers in the bonded material | very good |
| 4 (according to the invention) | polyalkylene-oxide dicyclohexyl-urethane (Production Example 2) [20 wt %] | Good, no separable layers in the bonded material | very good |
| 5 (according to the invention) | polyalkylene-oxide dibutyrate (Production Example 3) [25 wt %] | Good, no separable layers in the bonded material | very good |
| 6 (according to the invention) | polyalkylene-oxide diacetate (Production Example 4) [30 wt %] | Good, no separable layers in the bonded material | very good |
| 7 (according to the invention) | polyethylene-oxide dimethyl ether (Fluka Co. molecular weight 2,000) [25 wt %] | Slightly marbled, no separable layers in the bonded material | very good |

The experiments show that the materials in accordance with the present invention have outstanding storage-stability and also do not dissociate under increased pressure. When mixed using a static mixer, good mixing results are obtained. No layers can be seen which can be separated from each other, unlike in the comparative experiments. The mixing products of Experiments 3 to 7 meet all the requirements demanded of a dental-impression material according to ADA 19 (Test for elastomeric impression materials).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:
1. A polyether impression material comprising:
    (a) an aziridine-containing polyalkylene oxide in an amount of 20–80 wt%,
    (b) a sulfonium salt catalyst in an amount of 0.2–24 wt%, and
    (c) a mixing additive in an amount of 2–60 wt%,
in which the components (a) and (b) are spatially separate from each other, and the mixing additive (c) is a polyalkylene oxide derivative with a molecular weight over 300, which is chemically inert with the other components present and which contains no hydroxyl groups, acid groups, primary amino groups, ionic groups, halogen groups or groups capable of polymerization, and wherein the wt%'s provided are relative to the total weight of the impression material.

2. The polyether impression material according to claim 1, wherein the components (b) and (c) exist in a uniform mixture.

3. The polyether impression material according to claim 1, wherein the polyalkylene oxide derivative (c) has the following general formula:

$$R-C-[(CH_2)_n-(CHR')-O]_k-[(CH_2)_m-(CHR'')-O]_l-(CH_2)_m-(CHR'')-X-R \quad (I)$$

in which:
n = 1 to 6, and n can vary within the chain;
m = 1 to 6, and m can vary within the chain;
k, l = 2 to 500;
R', R'' = H, methyl, ethyl;
X = S, O, NH;
R = $C_{1-18}$-alkyl, carbonyl-$C_{1-17}$-alkyl, or a radical of the general Formula II:

$$\begin{array}{c} O \\ \parallel \\ -C-X-R''' \end{array} \quad (II)$$

R''' = $C_{1-18}$-alkyl, or $C_{1-18}$-aryl and X has the meaning indicated above;
with the proviso that the bracketed expressions indexed with the symbols K and l can be arranged in a regularly or irregularly alternating form, or in a block form.

4. The polyether impression material according to claim 1, wherein the polyalkylene oxide derivative (c) has an average molecular weight between 300 and 20,000.

5. In a method of preparing polyether impression materials, which utilizes mixing additives, the improvement comprising:
2-60 wt% of a polyalkylene oxide derivative mixing additive, which has a molecular weight above 300 and is chemically inert with the other components present in the impression materials and which does not contain hydroxyl groups, acid groups, primary amino groups, ionic groups, halogen groups or groups capable of polymerization, and wherein the wt% of the polyalkylene oxide derivative is relative to the total weight of the impression material prepared.

6. A process for preparing a polyether impression material, which comprises the step of mixing the following components (a)-(c) in a static mixing device:
(a) an aziridine-containing polyalkylene oxide in an amount of 20-80 wt%,
(b) a sulfonium salt catalyst in an amount of 0.2-24 wt%, and
(c) a mixing additive in an amount of 2-60 wt%,
in which the components (a) and (b) are spatially separate from each other, and the mixing additive (c) is a polyalkylene oxide derivative with a molecular weight over 300, which is chemically inert with the other components present and which contains no hydroxyl groups, acid groups, primary amino groups, ionic groups, halogen groups or groups capable of polymerization, and wherein the wt%'s provided are relative to the total weight of the impression material.

* * * * *